(12) United States Patent
Murray et al.

(10) Patent No.: US 11,642,492 B2
(45) Date of Patent: May 9, 2023

(54) FEMALE URINARY CATHETER DEPLOYMENT DEVICES AND METHODS OF USING THE SAME

(71) Applicant: Hollister Incorporated, Libertyville, IL (US)

(72) Inventors: Michael G. Murray, Ballina (IE); Roisin O'Brien, County Carlow (IE)

(73) Assignee: Hollister Incorporated, Libertyville, IL (US)

( * ) Notice: Subject to any disclaimer, the term of this patent is extended or adjusted under 35 U.S.C. 154(b) by 442 days.

(21) Appl. No.: 16/971,004

(22) PCT Filed: May 16, 2019

(86) PCT No.: PCT/US2019/032575
§ 371 (c)(1),
(2) Date: Aug. 19, 2020

(87) PCT Pub. No.: WO2019/245679
PCT Pub. Date: Dec. 26, 2019

(65) Prior Publication Data
US 2020/0391005 A1    Dec. 17, 2020

Related U.S. Application Data

(60) Provisional application No. 62/686,816, filed on Jun. 19, 2018.

(51) Int. Cl.
*A61M 25/00* (2006.01)
*A61F 5/455* (2006.01)
*A61M 25/01* (2006.01)

(52) U.S. Cl.
CPC ......... *A61M 25/0017* (2013.01); *A61F 5/455* (2013.01); *A61M 25/0111* (2013.01);
(Continued)

(58) Field of Classification Search
CPC .......... A61M 25/0017; A61M 25/0111; A61M 25/0113; A61M 2202/0496; A61M 2210/1092; A61F 5/455
See application file for complete search history.

(56) References Cited

U.S. PATENT DOCUMENTS

| 3,683,928 A | 8/1972 | Kuntz | |
| 4,652,259 A * | 3/1987 | O'Neil | ............... A61M 25/0111 600/581 |

(Continued)

OTHER PUBLICATIONS

International Search Report and Written Opinion of the International Searching Authority dated Aug. 27, 2020 for International Application No. PCT/US2019/032575.

*Primary Examiner* — Benjamin J Klein
*Assistant Examiner* — Hans Kaliher
(74) *Attorney, Agent, or Firm* — Cook Alex Ltd.

(57) ABSTRACT

A female urinary catheter deployment device includes a housing, an inner tip, an outer tip, a catheter, and an actuator. The outer tip is moved into the vicinity of the urethral opening of a female urethra. The outer tip is then moved from a closed condition to an open condition so as to expose a proximal end of the inner tip and position the proximal end of the inner tip within the urethra. The actuator is then moved with respect to the housing so as to proximally advance a proximal end of the catheter through and out of the proximal end of the inner tip and into the urethra. The proximal end of the catheter is further advanced through the urethra and into the bladder so as to drain urine from the bladder, through the catheter, and out of the housing.

13 Claims, 4 Drawing Sheets

(52) U.S. Cl.
CPC . *A61M 25/0113* (2013.01); *A61M 2202/0496* (2013.01); *A61M 2210/1092* (2013.01)

(56) References Cited

U.S. PATENT DOCUMENTS

| | | |
|---|---|---|
| 5,084,036 A | 1/1992 | Rosenbaum |
| 6,090,075 A | 7/2000 | House |
| 6,355,004 B1 | 3/2002 | Pedersen et al. |
| 6,544,240 B1 | 4/2003 | Borodulin et al. |
| 6,602,244 B2 | 8/2003 | Kavanagh et al. |
| 7,094,220 B2 | 8/2006 | Tanghoj et al. |
| 7,458,964 B2 | 12/2008 | Mosler et al. |
| 7,789,873 B2 | 9/2010 | Kubalak et al. |
| 7,985,217 B2 | 7/2011 | Mosler et al. |
| 9,168,354 B2 | 10/2015 | Hannon et al. |
| 9,199,057 B2 | 12/2015 | Nielsen |
| 9,345,855 B2 | 5/2016 | Young |
| 9,707,375 B2 | 7/2017 | Conway et al. |
| 9,782,563 B2 | 10/2017 | Palmer |
| 2009/0024111 A1 | 1/2009 | Borodulin et al. |
| 2010/0324540 A1* | 12/2010 | Paulen ............... A61M 25/002 604/544 |
| 2014/0324027 A1 | 10/2014 | House |
| 2016/0022959 A1 | 1/2016 | Schertiger et al. |
| 2016/0213880 A1* | 7/2016 | O'Flynn ............ A61M 25/0111 |
| 2016/0339205 A1 | 11/2016 | Foley et al. |
| 2017/0000978 A1 | 1/2017 | Murray et al. |

\* cited by examiner

FEMALE URINARY CATHETER DEPLOYMENT DEVICES AND METHODS OF USING THE SAME

RELATED APPLICATIONS

This application is a U.S. national stage application of PCT Patent Application Serial No. PCT/US2019/032575, filed May 16, 2019, which claims the benefit of and priority of U.S. Provisional Patent Application Ser. No. 62/686,816, filed Jun. 19, 2018, the contents of which are incorporated by reference herein.

DESCRIPTION

Technical Field

The present disclosure generally relates to female urinary catheters. More particularly, the present disclosure relates to devices for deploying female urinary catheters.

Background

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day.

Possible challenges associated with the use of a conventional female urinary catheter include properly positioning the catheter shaft in the vicinity of the urethral opening and the need to place two hands onto the catheter to fully insert the catheter shaft. Improper use of a urinary catheter may result in waste of the product (if the urinary catheter is discarded and replaced without being properly used) and infection (e.g., urinary tract infection) or contamination (e.g., bowel contamination). Accordingly, it would be advantageous to provide a self-catheterization system that overcomes these possible disadvantages of conventional catheters.

SUMMARY

There are several aspects of the present subject matter which may be embodied separately or together in the devices, systems, and/or methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a female urinary catheter deployment device includes a housing extending between proximal and distal ends, with an inner tip secured to the proximal end of the housing and including a proximal end positioned outside of the housing. An outer tip is associated with the proximal end of the housing and is movable from a closed condition to an open condition. A catheter is at least partially positioned within the housing, with an actuator secured to the catheter and movable with respect to the housing. The outer tip defines a protective enclosure for the proximal end of the inner tip when the outer tip is in the closed condition, while the inner tip defines a protective enclosure for a proximal end of the catheter when the outer tip is in the closed condition. A portion of the inner tip extends proximally through the outer tip so as to position the proximal end of the inner tip outside of the outer tip when the outer tip is in the open condition. The actuator is configured to be moved with respect to the housing to advance the proximal end of the catheter proximally through and out of the proximal end of the inner tip when the outer tip is in the open condition.

In another aspect, a catheterization method includes positioning an outer tip of a female urinary catheter deployment device in the vicinity of a urethral opening of a female urethra. The outer tip is moved from a closed condition to an open condition so as to advance at least a proximal end of an inner tip of the female urinary catheter deployment device proximally through the outer tip and into the female urethra. A proximal end of a catheter of the female urinary catheter deployment device is proximally advanced through the inner tip and into the female urethra and then further through the female urethra and into a bladder associated with the female urethra so as to drain urine from the bladder, through the catheter, and out of a housing of the female urinary catheter deployment device.

DETAILED DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
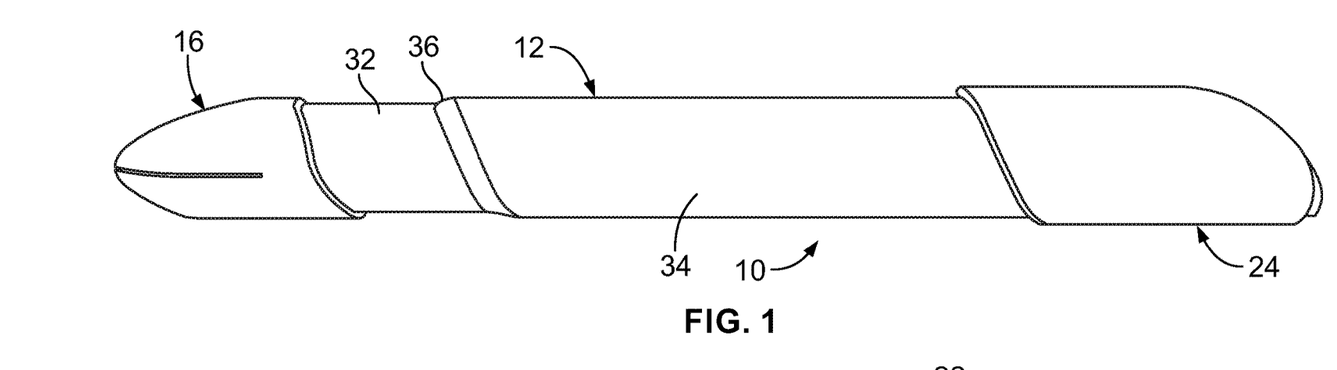
FIG. 1 is a side elevational view a female urinary catheter deployment device according to an aspect of the present disclosure.
Figure 2:
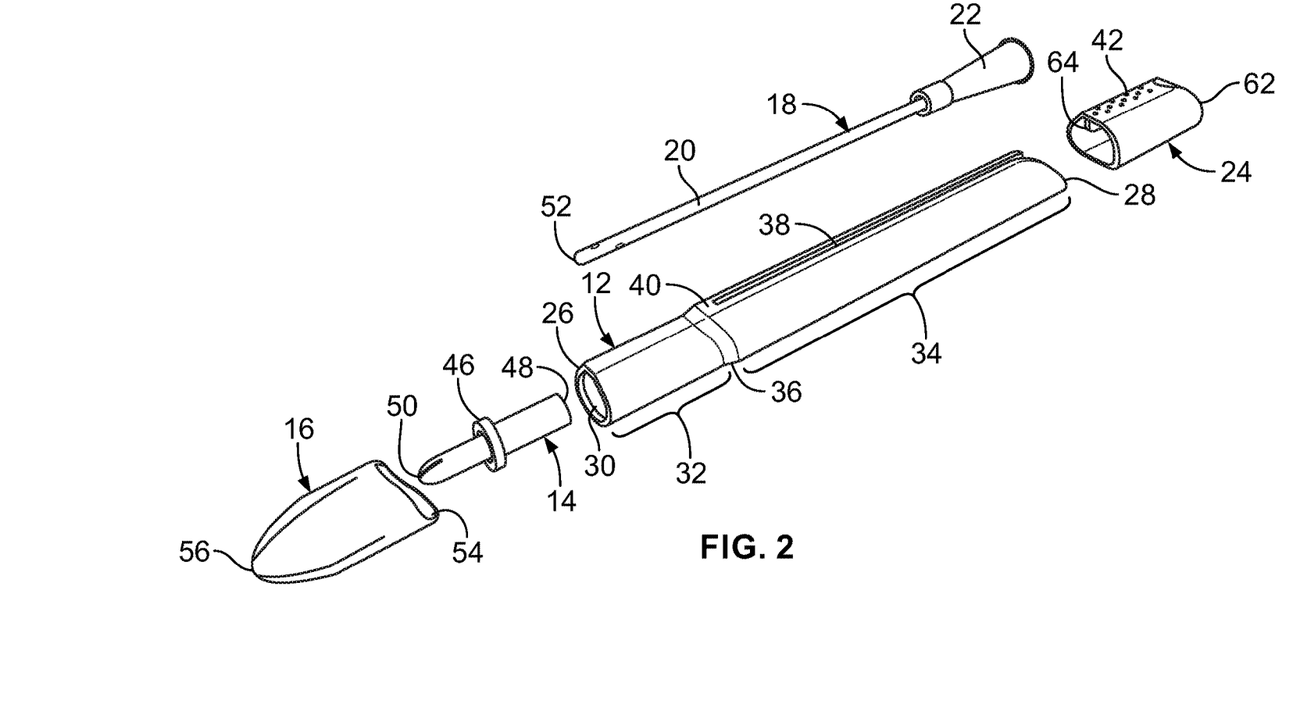
FIG. 2 is an exploded, perspective view of the female urinary catheter deployment device of FIG. 1.

Female urinary catheter deployment devices according to the present disclosure and their individual components may be variously configured without departing from the scope of the present disclosure, but in one embodiment, a female urinary catheter deployment device 10 is configured as shown in FIG. 1, with FIG. 2 showing individual components of the female urinary catheter deployment device 10.

In particular, the illustrated female urinary catheter deployment device 10 includes a housing or body 12, an inner tip or introducer tip 14 (FIG. 2), an outer tip or bumper tip 16, a catheter 18 (which is visible in FIG. 2 and may comprise a catheter shaft 20 connected at its distal end to a funnel 22), and an actuator or slider 24. FIGS. 3-6 show the relative positions of the various components of the female urinary catheter deployment device 10, along with showing their functions in performing a catheterization, as will be described in greater detail herein.

The housing 12 may be formed of a generally rigid material, such as a polyethylene material or other plastic material. The housing 12 extends between an at least partially open proximal end 26 and an at least partially open distal end 28, defining a hollow or open interior 30 (FIG. 2) to allow for the passage and/or positioning of other components of the female urinary catheter deployment device 10 and for the flow of urine through the housing 12. The housing 12 may be elongated and generally tubular. However, as in the illustrated embodiment, rather than having a perfectly tubular configuration (i.e., a uniform outer and inner diameter along its entire length), the housing 12 may have a varying diameter along its length. In the illustrated embodiment, the housing 12 includes a proximal portion 32 and a distal portion 34, with the proximal portion 32 being necked-down or otherwise having a smaller diameter or profile than the distal portion 34. In such a configuration, the proximal and distal portions 32 and 34 of the housing 12 may be separated by a shoulder 36 which (if provided) may limit movement of the outer tip 16, as will be described in greater detail herein.

Figure 7:
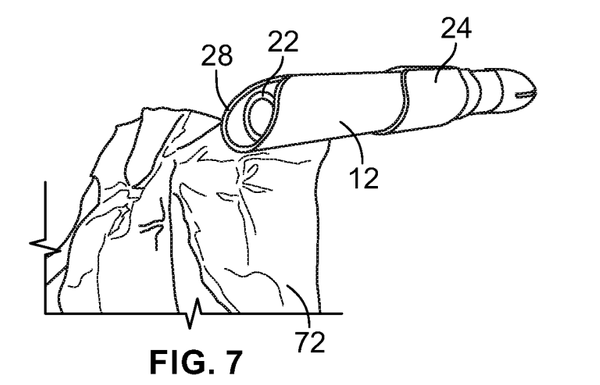
FIG. 7 is a perspective view of a collection bag that may be used in combination with the female urinary catheter deployment device of FIG. 1.
Figure 11:
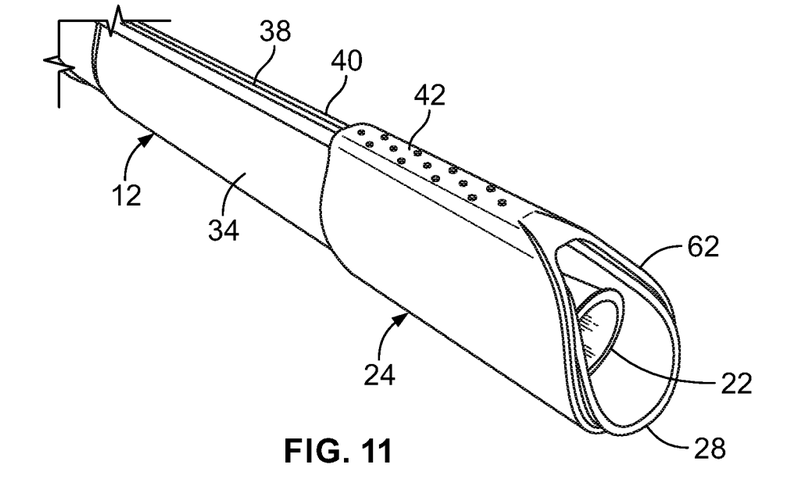
FIG. 11 is a perspective rear view of the female urinary catheter deployment device of FIG. 1.

In addition to having distinct proximal and distal portions 32 and 34, at least a portion of the housing 12 may have a non-circular cross-sectional shape. For example, in the illustrated embodiment, at least the distal portion 34 of the housing 12 has a teardrop-shaped profile or cross-sectional shape, as can be seen in FIGS. 7 and 11. The proximal portion 32 may also include a non-circular cross-sectional shape, such as a teardrop shape, which may be advantageous in restricting the orientation and movement of the outer tip 16 (e.g., by preventing rotation of the outer tip 16 with respect to the proximal portion 32), but it is also within the scope of the present disclosure for it to have a circular cross-sectional shape. It should be understood that the distal portion 34 of the housing 12 may also have a circular cross-sectional shape. Additionally, it should be understood that the cross-sectional shape of the housing 12 may vary along its length.

Depending on the configuration of the actuator 24 (which will be described in greater detail), a slot 38 may be defined in the housing 12, as can be seen in FIG. 2. In the illustrated embodiment, the slot 38 is elongated and extends longitudinally from the distal end 28 of the housing 12 along the distal portion 34 of the housing 12 without extending into the necked-down proximal portion 32. In other embodiments, the slot 38 may be omitted or differently configured. If a portion of the housing 12 (e.g., the distal portion 34) has a teardrop-shaped profile defining an apex 40, the slot 38 may be aligned with and extend along the apex 40, as in the illustrated embodiment. In such a configuration, the apex 40 and slot 38 may assist a user in properly orienting the female urinary catheter deployment device 10 during use. In particular, to avoid urine dripping through the slot 38, the housing 12 is preferably oriented so as to point the slot 38 upwardly (as in FIGS. 3-6), which prevents urine from dripping through the slot 38. The teardrop-shaped profile of the distal portion 34 of the housing 12, along with the visibility of the slot 38, signifies to the user that the housing 12 should be oriented with the apex 40 facing upwardly. As will be described in greater detail herein, the actuator 24 may have a teardrop-shaped profile and apex 42 to match the cross-sectional shape of the distal portion 34 of the housing 12, with the apex 42 of the actuator 24 being differently textured (as in FIG. 11) to further signify the proper orientation to the user. Furthermore, the distal end 28 of the housing 12, rather than defining a plane that is perpendicular to a central axis of the housing 12, may be angled (as in the illustrated embodiment) to define a spout, which may also signify the proper orientation to the user.

Figure 8:
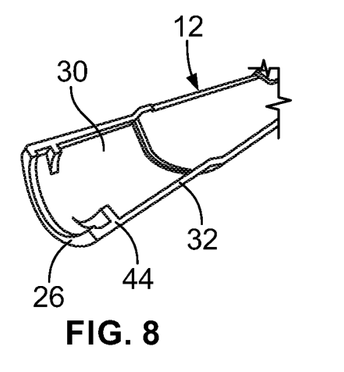
FIG. 8 is a cross-sectional detail view of a proximal end of a housing of the female urinary catheter deployment device of FIG. 1.
Figure 12:
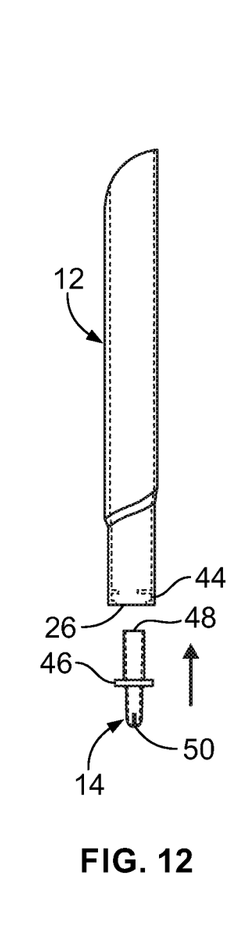
FIGS. 12-17 illustrate an exemplary method for assembling the female urinary catheter deployment device of FIG. 1.

As for the proximal portion 32 of the housing 12, it is shown in greater detail in FIG. 8. The proximal end 26 of the housing 12 may define a seat 44 to receive a portion of the inner tip 14 for securing the inner tip 14 in place with respect to the housing 12. In the illustrated embodiment, the inner tip 14 is configured as a conventional introducer tip of the type incorporated into the VaPro® touch-free hydrophilic intermittent catheter marketed by Hollister Incorporated of Libertyville, Ill., with an outwardly extending rim 46 (FIG. 2), in which case the seat 44 may be configured as a generally annular groove that receives at least a portion of the rim 46, as can be seen in FIGS. 3-6. In this case, the inner tip 14 may be associated to the housing 12 by relative movement of the inner tip 14 toward the housing 12 (as in FIG. 12), with the rim 46 deflecting as it passes into the seat 44 and then returning to its initial orientation to be mounted within the seat 44.

Figure 3:
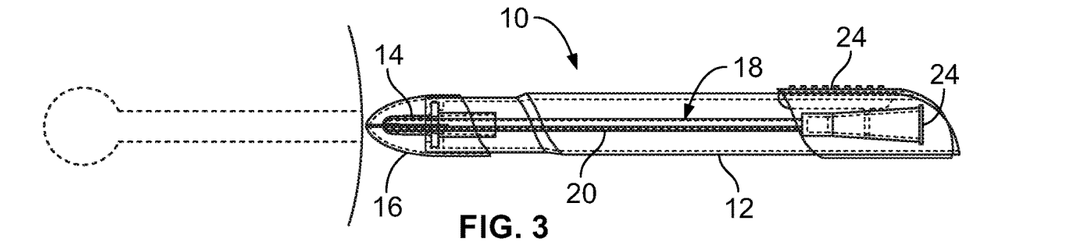
FIGS. 3-6 are cross-sectional views of the female urinary catheter deployment device of FIG. 1, illustrating a catheterization method according to an aspect of the present disclosure.
Figure 4:
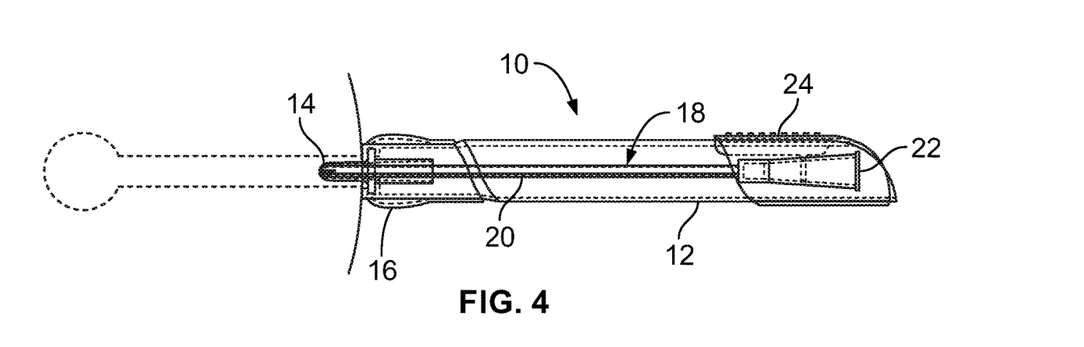

More particularly, the illustrated inner tip 14 extends between a distal end 48 and a proximal end 50, with the distal end 48 positioned within the housing 12 and the proximal end 50 positioned outside of the housing 12 when the inner tip 14 is properly associated to the proximal end 26 of the housing 12 (FIGS. 3-7). The inner tip 14 (as will be described in greater detail herein) is sized and configured for insertion into a female urethra (up to the rim 46) prior to advancement of a proximal end 52 of the catheter shaft 20 into the urethra, as shown in FIG. 4. Accordingly, it may be advantageous for the inner tip 14 to be formed of a soft, transparent material for improved comfort and visibility. The proximal end 50 of the inner tip 14 may include an aperture or opening that may be moved from a closed configuration (in which there is no object positioned within the opening, as in FIGS. 3 and 4) to an open configuration (in which the catheter shaft 20 is partially positioned within or extending through the opening, with a portion of the catheter shaft 20 positioned within the inner tip 14 and another portion positioned outside of the inner tip 14, as in FIGS. 5 and 6). In one embodiment, the proximal opening of the inner tip 14 may be provided as a slit opening with one or more slits or cuts defining a plurality of deformable petals that may be moved to define the aforementioned open and closed configurations. In other embodiments, the opening may be differently configured, provided that it is configured to allow passage of the catheter shaft 20 therethrough.

Alternatively, rather than employing an inner tip according to conventional design, it may be advantageous to employ a modified configuration. In particular, a conventionally designed introducer tip has a relatively large rim that may be well-suited for male use, but less well-suited for female use (by requiring the lips of the labia to be spread farther apart). In a modified configuration, the inner tip may have the same general configuration, but a nominal (or at least smaller) rim that does not extend as far away from the base or body of the inner tip. By such a configuration, the rim may still be secured within the seat 44 of the housing 12, but the housing 12 (and particularly the necked-down proximal portion 32) and the outer tip 16 may be provided with smaller outer diameters, which allows for easier catheterization by requiring less spreading of the lips of the labia.

Similar to the inner tip 14, the outer tip 16 is also associated with the proximal end 26 of the housing 12. However, whereas the inner tip 14 is partially positioned within the proximal end 26 of the housing 12, the proximal end 26 of the housing 12 is instead positioned within the outer tip 16 when the outer tip 16 is in the closed condition of FIGS. 1 and 3. The outer tip 16 may be variously configured without departing from the scope of the present disclosure, but in any case defines a protective enclosure for the proximal end 50 of the inner tip 14 while the outer tip 16 is in its closed condition. By providing such a protective enclosure, the outer tip 16 allows a user to properly position the female urinary catheter deployment device 10 in the vicinity of the urethral opening (as will be described in greater detail) without bringing the proximal end 50 of the inner tip 14 into contact with any body surface outside of the urethra, thus reducing the risk of infection and/or contamination.

As will be described in greater detail herein, the outer tip 16 is configured to move from a closed condition (as in FIGS. 1 and 3) to an open condition (as in FIGS. 4-6, such that it may be advantageous for the outer tip 16 to be formed of a deformable material or be otherwise configured for movement from a closed condition to an open condition. The exact configuration of the outer tip 16 in its open and closed conditions may vary without departing from the scope of the present disclosure, such that the composition of the outer tip 16 may also vary to accommodate the transition from the open condition to the open condition. It is also within the scope of the present disclosure for the outer tip 16 to either be configured for movement between the closed and open conditions or for movement only from the closed condition to the open condition, which may also affect the composition of the outer tip 16. However, in the illustrated embodiment, the outer tip 16 is formed of a deformable material, such as a polyurethane rubber material, which allows for the outer tip 16 to be deformed in moving from the closed condition to the open condition.

The illustrated embodiment of the outer tip 16 extends between a distal end 54 and a proximal end 56, with the proximal end 56 positioned proximally of the housing 12 and the inner tip 14 when the outer tip 16 is in its closed condition. At least the distal end 54 of the outer tip 16 (and, more preferably, a distal portion of the outer tip 16) surrounds the proximal end 26 and part of the proximal portion 32 of the housing 12 to enclose the proximal end 26 of the housing 12 and the portion of the inner tip 14 extending outside of the housing 12.

Figure 5:
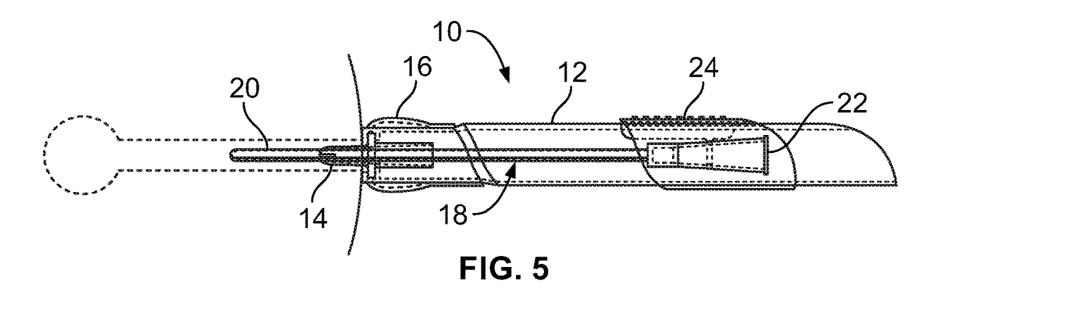
Figure 6:
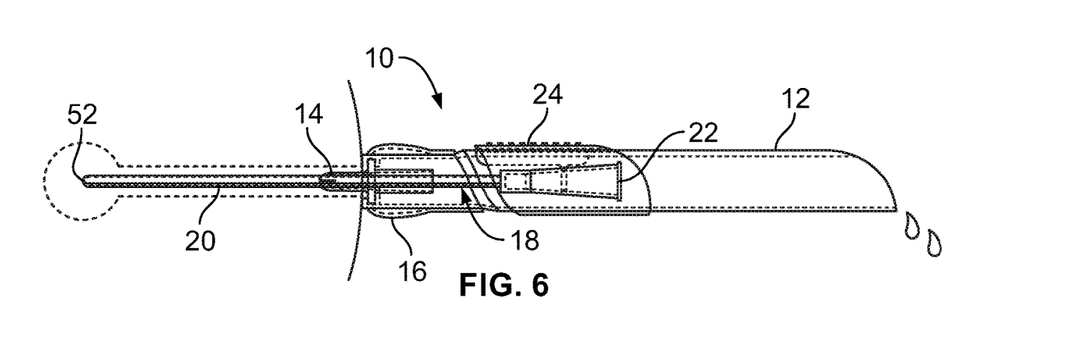

The proximal end 56 of the outer tip 16 may be configured similarly to the proximal end 50 of the inner tip 14, with an aperture or opening that may be moved from its closed condition (in which there is no object positioned within the opening, as in FIGS. 1 and 3) to an open condition (in which at least the inner tip 14 is partially positioned within or extending through the opening for advancement into a female urethra, as in FIGS. 4-6). In one embodiment, the proximal opening of the outer tip 16 may be provided as a slit opening with one or more slits or cuts defining a plurality of deformable petals that may be moved to define the aforementioned open and closed conditions. In other embodiments, the opening may be differently configured, provided that it is configured to move between a closed condition protecting the inner tip 14 and an open condition allowing passage of the inner tip 14 therethrough.

In the illustrated embodiment, the outer tip 16 has a maximum outer diameter that is greater than the diameter of a female urethral opening, which prevents the outer tip 16 from being advanced into the urethra when the female urinary catheter deployment device 10 is pressed against the urethral opening. Rather than advancing into the urethra, such movement of the female urinary catheter deployment device 10 causes the outer tip 16 to move distally with respect to the housing 12, deforming from its closed condition (FIG. 3) to its open condition (FIG. 4). If the housing 12 includes a shoulder 36 separating the proximal and distal portions 32 and 34 of the housing 12, the outer tip 16 may be configured to move distally along the proximal portion 32 of the housing 12 until the distal end 54 of the outer tip 16 contacts the shoulder 36 to prevent further distal advancement of the outer tip 16 along the housing 12. In other embodiments, other approaches may be taken to defining a final open condition assumed by the outer tip 16 just prior to and during advancement of the catheter shaft 20 through a female urethra.

Figure 9:
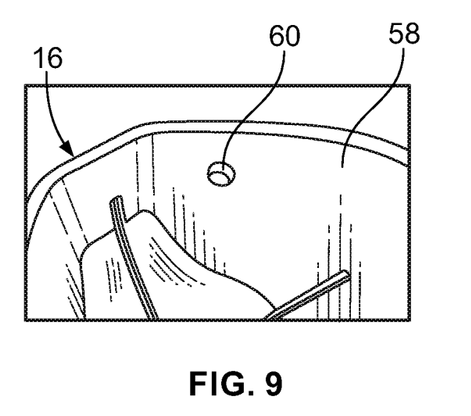
FIG. 9 is a detail view of an inner surface of an outer tip of the female urinary catheter deployment device of FIG. 1.

The outer tip 16 may be secured or associated to the proximal end 26 of the housing 12 according to any suitable approach. In the illustrated embodiment, in which the outer tip 16 is movable along a portion of the housing 12, an inner surface 58 of the outer tip 16 includes an inwardly extending projection or dimple or formation 60 (FIG. 9) that is received by a cavity (not illustrated) defined in the proximal portion 32 of the housing 12. The formation-cavity combination prevents the outer tip 16 from moving proximally away from its closed condition, thereby preventing dissociation of the outer tip 16 from the housing 12. The cavity may define a track in which the formation 60 is constrained to travel as the outer tip 16 moves from its closed condition to its open condition, thus guiding and ensuring proper movement of the outer tip 16 from the closed condition to the open condition. Alternatively, rather than defining a track, the outer tip 16 (or at least the formation 60) may be deformable to allow the formation 60 to be unseated from the cavity when moving the outer tip 16 from its closed condition to its open condition, with such a cavity only serving to temporarily retain the outer tip 16 in the closed condition, without also defining a guide.

Figure 10:
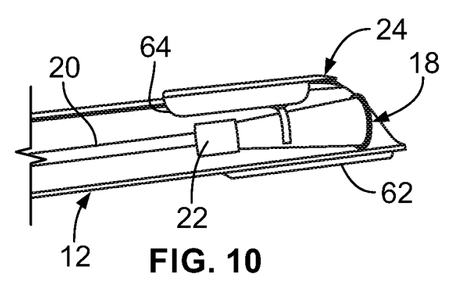
FIG. 10 is a detail view of a distal end of the housing of the female urinary catheter deployment device of FIG. 1, with a portion of the housing broken away to show an actuator and catheter partially positioned within the housing.

Turning now to the actuator 24, it is secured to the catheter 18 and configured to move the catheter 18 with respect to the housing 12. The actuator 24 may be configured for different movement to cause the desired movement of the catheter 18. In the illustrated embodiment, the actuator 24 is configured as a slider, which may be moved proximally along the housing 12 to effect proximal movement of the catheter 18 with respect to the housing 12. In such an embodiment, the actuator 24 may comprise a body 62 positioned outside of the housing 12, with a clip 64 extending radially inwardly from the body 62 (FIG. 10) through the slot 38 defined in the distal portion 34 of the housing 12. It may be advantageous for the body 62 of the actuator 24 to have a profile that matches the profile of the outer surface of the portion of the housing 12 over which it slides to allow for smooth movement of the actuator 24 (which may be formed of a generally rigid material, such as a polyethylene material or other plastic material) over the housing 12. Thus, in the illustrated embodiment, the body 62 of the actuator 24 has a teardrop-shaped profile and apex 42 (FIGS. 2 and 11) to match the cross-sectional shape of the distal portion 34 of the housing 12. As described previously, the apex 42 of the actuator 24 may be differently textured (as in FIG. 11) to signify the proper orientation of the female urinary catheter deployment device 10 to the user.

Figure 13:
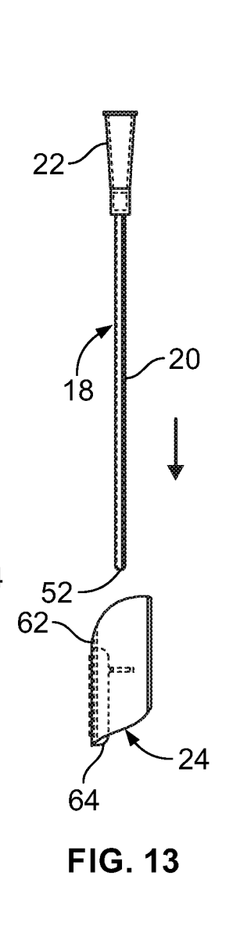

As for the clip 64, it engages the catheter 18 to ensure that any movement of the actuator 24 is matched by the same movement of the catheter 18. In the illustrated embodiment, in which the catheter 18 is configured according to conventional design and comprises a catheter shaft 20 connected at its distal end to a funnel 22, the clip 64 is secured to the funnel 22 of the catheter 18. The free end of the clip 64 (i.e., the end opposite the location at which the clip 64 meets the body 62, or the bottom end in the orientation of FIG. 10) may be generally arcuate or C-shaped, with relative movement of the actuator 24 with respect to the catheter 18 (with the catheter shaft 20 passing through the clip 64 before the funnel 22, as in FIG. 13) eventually causing a friction or interference fit between the clip 64 and the funnel 22. Alternatively, rather than relying on a friction fit, an adhesive may be provided to secure the clip 64 to the catheter 18 (in addition to or instead of the friction fit), or some other joinder means may be employed to replace or to supplement a friction fit. Additionally, it should be understood that the illustrated configuration is merely exemplary and that the clip may be differently configured without departing from the scope of the present disclosure. For example, rather than being secured to the funnel 22, the clip may instead be secured to the catheter shaft 20 or to both the funnel 22 and the catheter shaft 20.

Figure 14:
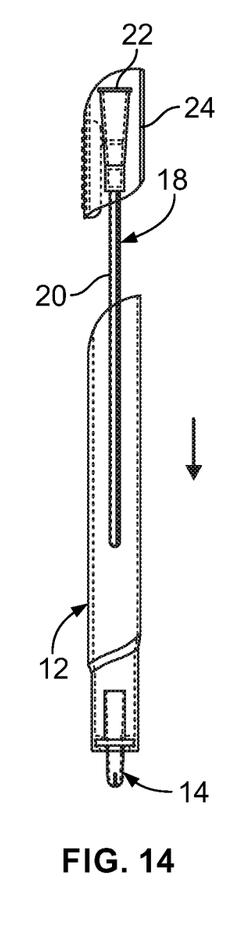

In the illustrated embodiment, the slot 38 extends to the distal end 28 of the housing 12, in which case relative movement of the housing 12 and the assembled actuator 24 and catheter 18 (FIG. 14) advances the clip 64 into the slot 38, with the catheter shaft 20 entering the interior 30 of the housing 12 and the actuator body 62 remaining outside of the housing 12. In the illustrated embodiment, the inner tip 14 is secured to the proximal end 26 of the housing 12 prior to the actuator 24 and catheter 18 being associated to the housing 12, such that the presence of the closed proximal end 50 of the inner tip 14 prevents over-insertion of the actuator 24 and catheter 18 into the housing 12. It should be understood that the assembly step of FIG. 14 is merely exemplary and that the conjoined actuator 24 and catheter 18 may be associated to the housing 12 in a different manner. For example, if the slot 38 does not extend to the distal end 28 of the housing 12, the housing 12 may be provided in two parts, with the clip 64 being placed into the (temporarily) open slot before the two parts are secured together to trap the clip 64 within the closed slot.

Figure 15:
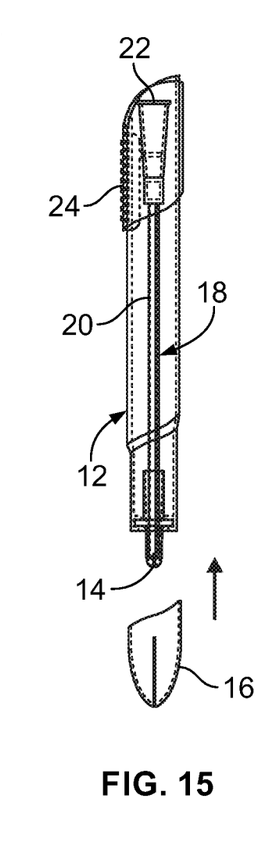
Figure 16:
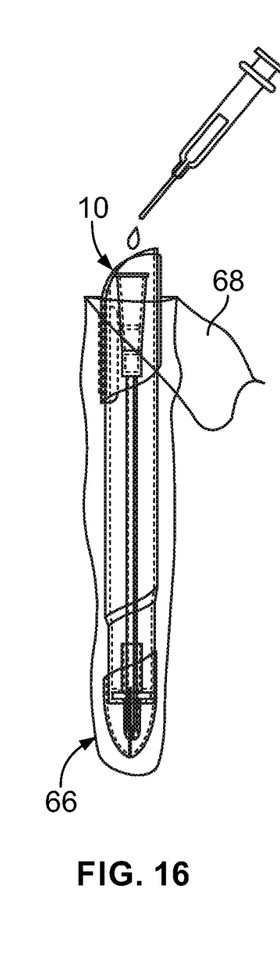
Figure 17:
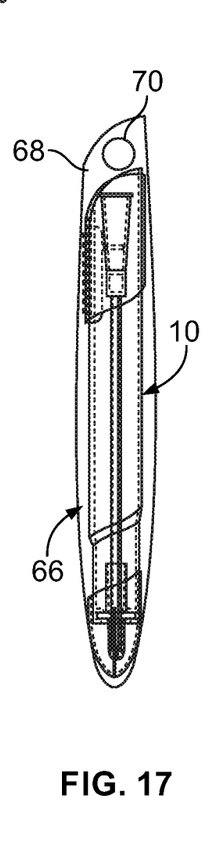

As shown in FIG. 15, the outer tip 16 may be associated to the proximal end 26 of the housing 12 after the conjoined actuator 24 and catheter 18 have been associated to the housing 12, as the last step in assembling the female urinary catheter deployment device 10. Alternatively, the outer tip 16 may be associated to the housing 12 before the actuator 24 and catheter 18. Regardless of the particular order of assembly, the assembled female urinary catheter deployment device 10 may be inserted into a partially sealed package 66 (FIG. 16). One end or portion 68 of the package 66 (the end or portion positioned adjacent to the distal end 28 of the housing 12) may remain open to allow for injection of a fluid into the housing 12. In such an embodiment, at least a portion of the inner surface 58 of the outer tip 16 and at least a portion of the surface of the catheter shaft 20 may include a hydrophilic coating, in which case the fluid reacts with the hydrophilic coating to lubricate the associated portions of the outer tip 16 and catheter shaft 20. The open end or portion 68 of the package 66 may be subsequently sealed or otherwise closed (FIG. 17), thereby providing the user with a pre-lubricated catheter shaft 20 when the package 66 is opened.

Turning now to use of the female urinary catheter deployment device 10 for catheterization, it is first removed from its package 66 by the user. In one embodiment, the package 66 may include a loop hole or other formation 70 for ease of opening, with the formation 70 preferably being positioned adjacent to the distal end 28 of the housing 12 (i.e., being positioned at the end or portion 68 of the package 66 that is sealed after addition of fluid) to ensure that the user grips the actuator 24 or housing 12, rather than gripping the outer tip 16 at the opposite end.

While gripping the housing 12 with one hand, the user spreads the lips of the labia with the other hand, and then moves the outer tip 16 into the vicinity of the urethral opening, as in FIG. 3. The outer tip 16 is not advanced into the urethra opening, so the risk of contamination and/or infection resulting from contact between the outer tip 16 and some other body surface during positioning of the female urinary catheter deployment device 10 is minimized.

With the outer tip 16 in position at the urethral opening, the user presses the housing 12 toward the urethral opening to move the outer tip 16 from its closed condition (FIG. 3) to its open condition (FIG. 4). This same movement that moves the outer tip 16 to its open condition also advances the proximal end 50 of the inner tip 14 through the opening of the outer tip 16 and into the urethra.

The user then moves the actuator 24 proximally with respect to the housing 12 to advance the proximal end 52 of the catheter shaft 20 through the opening of the inner tip 14 and into the urethra, as in FIG. 5. The presence of the inner tip 14 reduces the risk of infection by allowing the catheter shaft 20 to bypass bacteria in the first 15 mm of the urethra.

The user continues to move the actuator 24 proximally with respect to the housing 12 to advance the proximal end 52 of the catheter shaft 20 through the urethra and into the bladder, as in FIG. 6. In one embodiment, the slot 38 may be configured to have a length approximately equal to the length of the female urethra, such that the user needs only slide the actuator 24 the entire length of the slot 38 to ensure proper positioning of the proximal end 52 of the catheter shaft 20.

With the proximal end 52 of the catheter shaft 20 properly positioned within the bladder, urine drains from the bladder into the catheter shaft 20 via one or more openings or eyes at or adjacent to the proximal end 52 of the catheter shaft 20. The urine flows through the catheter shaft 20, out of the catheter 18 (via the funnel 22, if provided), and into the housing 12, where it finally flows out of the housing 12 and into a disposal receptacle (e.g., a collection bag 72, as in FIG. 7, or a toilet).

When the bladder has been drained of urine, the user removes the female urinary catheter deployment device 10 from the urethra for disposal, such as in a garbage can. The user may retract the catheter shaft 20 into the housing 12 by moving the actuator 24 distally with respect to the housing 12 or may remove and dispose of the female urinary catheter deployment device 10 without retracting the catheter shaft 20.

Female urinary catheter deployment devices according to the present disclosure have several advantages over conventional female urinary catheters. For example, female urinary catheter deployment devices according to the present disclosure may be operated using one hand, while the other hand holds back the lips of the labia. This is in comparison to conventional female urinary catheters, which may require the user to have both hands on the catheter during use. Additionally, female urinary catheter deployment devices according to the present disclosure may be used with one continuous movement (to open the outer tip 16 and then advance the catheter shaft 20 through the urethra), which naturally moves the hand away from the region where urine flows out of the housing 12.

It should be understood that the female urinary catheter deployment device 10 illustrated in FIG. 1 is merely exemplary and that female urinary catheter deployment devices may be differently configured without departing from the scope of the present disclosure. For example, while it is preferred for the female urinary catheter deployment device 10 to be provided with an inner tip 14, it should be understood that the inner tip 14 may be omitted. In such an embodiment, movement of the outer tip 16 from its closed condition to its open condition exposes the proximal end 52 of the catheter shaft 20 for direct insertion into the urethra. In the embodiment of FIG. 1, the inner tip 14 may provide a centering or orienting feature for the catheter shaft 20, such that, in the absence of the inner tip 14, it may be advantageous for the housing to include a formation or feature that centers or otherwise properly orients the catheter shaft 20 within the housing 12.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A female urinary catheter deployment device, comprising:
    a housing extending between proximal and distal ends;
    an inner tip secured to the proximal end of the housing and including a proximal end positioned outside of the housing;
    an outer tip associated with the proximal end of the housing and movable from a closed condition to an open condition;
    a catheter at least partially positioned within the housing; and
    an actuator secured to the catheter and movable with respect to the housing, wherein
        the outer tip defines a protective enclosure for the proximal end of the inner tip when the outer tip is in the closed condition,
        the inner tip defines a protective enclosure for a proximal end of the catheter when the outer tip is in the closed condition,
        a portion of the inner tip extends proximally through the outer tip so as to position the proximal end of the inner tip outside of the outer tip when the outer tip is in the open condition, and
        the actuator is configured to be moved with respect to the housing to advance the proximal end of the catheter proximally through and out of the proximal end of the inner tip when the outer tip is in the open condition.

2. The female urinary catheter deployment device of claim 1, wherein
    the catheter comprises a catheter shaft and a funnel secured to a distal end of the catheter shaft, and
    the actuator is secured to the funnel.

3. The female urinary catheter deployment device of claim 1, wherein the actuator comprises a slider configured to move proximally along the housing.

4. The female urinary catheter deployment device of claim 1, wherein
    the housing defines a slot, and
    the actuator includes a body positioned outside of the housing and a clip extending from the body, through the slot, and into an interior of the housing to engage the catheter.

5. The female urinary catheter deployment device of claim 4, wherein the body is generally teardrop-shaped and includes an apex aligned with the slot.

6. The female urinary catheter deployment device of claim 5, wherein the apex is differently textured than other portions of the body.

7. The female urinary catheter deployment device of claim 1, wherein the outer tip is configured to be deformed in moving from the closed condition to the open condition.

8. The female urinary catheter deployment device of claim 1, wherein the outer tip is configured to move distally along the housing in moving from the closed condition to the open condition.

9. The female urinary catheter deployment device of claim 8, wherein
    the housing includes a necked-down proximal portion separated from a distal portion of the housing by a shoulder, and
    the outer tip is configured to move distally along the proximal portion of the housing and into contact with the shoulder in moving from the closed condition to the open condition.

10. The female urinary catheter deployment device of claim 1, further comprising a collection bag associated with the distal end of the housing.

11. The female urinary catheter deployment device of claim 1, wherein the outer tip is formed of a polyurethane rubber material.

12. The female urinary catheter deployment device of claim 1, further comprising a hydrophilic coating applied to at least a portion of an inner surface of the outer tip.

13. The female urinary catheter deployment device of claim 1, wherein
    the proximal end of the housing includes a generally annular groove, and
    the inner tip includes an outwardly extending rim at least partially received by the groove.

\* \* \* \* \*